(12) United States Patent
Clement

(10) Patent No.: US 7,530,810 B2
(45) Date of Patent: May 12, 2009

(54) DENTAL FIXTURE IMPLANTATION SYSTEM AND ASSOCIATED METHOD

(76) Inventor: Milton A. Clement, 1860 Summerland Ave., Winter Park, FL (US) 32789

( * ) Notice: Subject to any disclaimer, the term of this patent is extended or adjusted under 35 U.S.C. 154(b) by 0 days.

(21) Appl. No.: 11/468,480

(22) Filed: Aug. 30, 2006

(65) Prior Publication Data

US 2008/0057472 A1 Mar. 6, 2008

(51) Int. Cl.
*A61C 13/08* (2006.01)
*A61C 8/00* (2006.01)
*A61F 2/28* (2006.01)

(52) U.S. Cl. .................. 433/173; 433/172; 433/174; 433/175; 433/176; 433/225; 433/220; 433/221; 623/16.11

(58) Field of Classification Search .......... 433/18, 433/172–176, 201.1; 623/16.11, 17.17; 427/2.26, 427/2.29
See application file for complete search history.

(56) References Cited

U.S. PATENT DOCUMENTS

| | | | |
|---|---|---|---|
| 2,721,387 A * | 10/1955 | Ashuckian | 433/173 |
| 3,465,441 A | 9/1969 | Linkow | 32/10 |
| 3,683,501 A | 8/1972 | Edelman | 32/10 |
| 4,079,515 A | 3/1978 | Friedman | 32/10 |
| 4,223,412 A | 9/1980 | Aoyagi et al. | 3/1.9 |
| 4,253,833 A | 3/1981 | Edelman | 433/173 |
| 4,302,188 A | 11/1981 | Driskell | 433/173 |
| 4,492,577 A | 1/1985 | Farris et al. | 433/201 |
| 4,511,335 A | 4/1985 | Tatum, Jr. | 433/173 |
| 4,522,596 A | 6/1985 | Ashkinazy | 433/173 |
| 4,636,216 A | 1/1987 | Tatum | 623/16 |
| 4,752,294 A | 6/1988 | Lundgren | 623/11 |
| 4,773,858 A * | 9/1988 | Marquez | 433/173 |
| 4,789,338 A | 12/1988 | Eisenmann | 433/181 |
| 4,799,886 A | 1/1989 | Wimmer | 433/176 |
| 4,818,559 A | 4/1989 | Hama et al. | 427/2 |
| 4,997,383 A | 3/1991 | Weiss et al. | 433/176 |
| 5,102,336 A | 4/1992 | Linkow | 433/176 |
| 5,108,289 A * | 4/1992 | Fukuyo | 433/173 |
| 5,110,293 A | 5/1992 | Linkow | 433/176 |
| 5,116,226 A | 5/1992 | Linkow | 433/176 |

(Continued)

FOREIGN PATENT DOCUMENTS

JP 5-64646 3/1993

(Continued)

*Primary Examiner*—Cris L Rodriguez
*Assistant Examiner*—Yogesh Patel
(74) *Attorney, Agent, or Firm*—Allen, Dyer, Doppelt, Milbrath & Gilchrist, P.A.

(57) ABSTRACT

A dental implantation system is for securing a dental prosthesis in a patient's jawbone including an alveolar bone, a basal bone adjacent the alveolar bone, and a neurovascular bundle running through the jawbone. The dental implantation system may include a dental implant fixture having an elongate shape and including an upper portion to be positioned in the alveolar bone to receive the dental prosthesis and defining a first axis. The dental implant fixture may also include a lower portion to be positioned in the basal bone and defining a second axis. The dental implant fixture may further include an intermediate offset-defining portion between the upper portion and the lower portion to define an offset between the first axis and the second axis so that the lower portion avoids the neurovascular bundle.

21 Claims, 3 Drawing Sheets

U.S. PATENT DOCUMENTS

| | | | |
|---|---|---|---|
| 5,123,842 A | 6/1992 | Roberts | 433/173 |
| 5,152,687 A | 10/1992 | Amino | 433/173 |
| 5,196,016 A | 3/1993 | Buser et al. | 606/72 |
| 5,219,286 A | 6/1993 | Hader | 433/172 |
| 5,246,370 A | 9/1993 | Coatoam | 433/173 |
| 5,324,199 A | 6/1994 | Branemark | 433/174 |
| 5,342,199 A | 8/1994 | Gillespie | 433/173 |
| 5,372,503 A | 12/1994 | Elia | 433/215 |
| 5,397,235 A * | 3/1995 | Elia | 433/173 |
| 5,511,565 A | 4/1996 | Syers | 128/898 |
| 5,538,426 A | 7/1996 | Harding et al. | 433/172 |
| 5,542,847 A | 8/1996 | Margulies | 433/173 |
| 5,700,479 A | 12/1997 | Lundgren | 424/435 |
| 5,725,376 A | 3/1998 | Poirier | 433/172 |
| 5,769,898 A | 6/1998 | Jisander | 623/16 |
| 5,785,525 A | 7/1998 | Weissman | 433/174 |
| 5,816,809 A | 10/1998 | Sapkos | 433/172 |
| 5,839,899 A | 11/1998 | Robinson | 433/215 |
| 5,873,721 A | 2/1999 | Willoughby | 433/173 |
| 5,879,161 A | 3/1999 | Lazzara | 433/173 |
| 5,885,078 A | 3/1999 | Cagna et al. | 433/173 |
| 5,888,065 A | 3/1999 | Sussman | 433/76 |
| 5,888,068 A | 3/1999 | Lans et al. | 433/181 |
| 5,967,783 A | 10/1999 | Ura | 433/174 |
| 5,976,142 A | 11/1999 | Chin | 606/73 |
| 5,984,681 A | 11/1999 | Huang | 433/174 |
| 6,030,218 A | 2/2000 | Robinson | 433/173 |
| 6,039,568 A | 3/2000 | Hinds | 433/175 |
| 6,050,820 A | 4/2000 | Lans et al. | 433/181 |
| 6,152,737 A | 11/2000 | Beaty et al. | 433/172 |
| 6,168,435 B1 | 1/2001 | Beaty et al. | 433/172 |
| 6,168,436 B1 | 1/2001 | O'Brien | 433/173 |
| 6,205,837 B1 | 3/2001 | Sapkos | 73/1.12 |
| 6,234,797 B1 | 5/2001 | Ura | 433/174 |
| 6,238,214 B1 | 5/2001 | Robinson | 433/215 |
| 6,244,868 B1 | 6/2001 | Schappert | 433/173 |
| 6,296,483 B1 | 10/2001 | Champleboux | 433/75 |
| 6,319,006 B1 | 11/2001 | Scherer et al. | 433/215 |
| 6,343,930 B1 | 2/2002 | Beaty et al. | 433/173 |
| 6,394,801 B2 | 5/2002 | Christi et al. | 433/24 |
| 6,450,812 B1 | 9/2002 | Laster et al. | 433/173 |
| 6,814,575 B2 | 11/2004 | Poirier | 433/75 |
| 6,869,283 B2 | 3/2005 | Sussman | 433/76 |
| 2001/0012607 A1 | 8/2001 | Robinson | 433/215 |
| 2002/0028418 A1 | 3/2002 | Farag et al. | 433/29 |
| 2002/0031747 A1 | 3/2002 | Laster et al. | 433/173 |
| 2004/0161725 A1 | 8/2004 | Clement | 433/176 |
| 2004/0185419 A1* | 9/2004 | Schulter et al. | 433/173 |
| 2005/0037320 A1 | 2/2005 | Poirier | 433/173 |

FOREIGN PATENT DOCUMENTS

| | | |
|---|---|---|
| WO | 9403121 | 2/1994 |

* cited by examiner

DENTAL FIXTURE IMPLANTATION SYSTEM AND ASSOCIATED METHOD

FIELD OF THE INVENTION

The invention relates to the field of dentistry, and, more particularly, to dental implants and related methods.

BACKGROUND OF THE INVENTION

A dental implant can be surgically implanted in a dental patient and a prosthesis mounted on the implant to replace a natural tooth that the patient has lost due to decay or injury. Such a dental prosthesis can be an artificial tooth or crown that affixes to a post that is secured to the patient's alveolar ridge, the bone ridge that forms the borders of the upper and lower jaws and contains the sockets of the patient's teeth.

Some of the problems with prior art dental implant fixtures are explained with reference to FIG. 1. A patient's jawbone 10 includes a neurovascular bundle 12 or a sinus that limits the depth at which a dental implant fixture 14 can be positioned into the jawbone thereby limiting the anchor strength of the dental implant fixture. Another frequently observed problem related to the implantation of a dental prosthesis is that when a prosthesis is needed by a patient, it usually is needed where the patient has also experienced bone loss or deterioration in the alveolar ridge. When, as a result of disease or injury, bone loss has occurred in or around where a dental prosthesis is needed, it may be that there is not enough bone in which to implant a dental implant fixture in the alveolar ridge. As a result, the anchor strength of the dental implant fixture 14 will be diminished because the dental implant fixture 14 will need to be smaller in size to compensate for the narrow ridge width. Conventional devices and methods have sought to address these problems through different types of dental implant fixtures with each requiring a succession of surgical procedures.

For example, U.S. Pat. No. 5,324,199 to Branemark discloses a dental fixture anchored below the neurovascular bundle in the basal bone. The dental fixture includes a cylindrical shaft having opposing threaded ends and a thread-free midsection. The dental fixture is inserted into a prepared hole in the jawbone with the nerve being lifted out of the way. After the dental fixture is positioned, the nerve is repositioned against the thread-free midsection. At a later date when the dental fixture becomes integrated into the jawbone, the dental prosthesis can be fitted on the dental fixture.

Similarly, U.S. Pat. Nos. 5,725,376 and 6,814,575 and U.S. Published Application 2005/0037320 to Poirier disclose a computer system for modeling a patient's teeth and jawbone. The model is used to produce a drill guide to aid the surgeon in preparing the implant hole for a dental fixture in the patient's jawbone that avoids the neurovascular bundle. The model is also used to produce the dental fixture inserted into the implant hole. A dental prosthesis is attached to the dental fixture at a date after the dental fixture is implanted into the patient's jawbone.

U.S. Pat. No. 6,319,006 to Scherer et al. discloses modeling a patient's jawbone using an x-ray image superimposed on a three dimensional image to map out an implant hole for a dental fixture. The map is used to locate the nerve thereby setting a lower limit for the implant hole and to produce a drill guide used to create the implant hole.

Unfortunately, such conventional techniques and dental fixtures require a patient to make multiple visits to the attending physician and/or may require a lengthy interval between the initial operation and the final installation of the dental prosthesis.

SUMMARY OF THE INVENTION

In view of the foregoing background, it is therefore an object of the invention to provide a dental implantation system that permits a dental fixture carrying a dental prosthesis to be implanted below the level of the neurovascular bundle.

This and other objects, features, and advantages in accordance with the invention are provided by a dental implantation system that may secure a dental prosthesis in a patient's jawbone. The patient's jawbone includes an alveolar bone, a basal bone adjacent the alveolar bone, and a neurovascular bundle running through the jawbone. The dental implantation system may include a dental implant fixture having an elongate shape and including an upper portion to be positioned in the alveolar bone to receive the dental prosthesis and defining a first axis. The dental implant fixture may also include a lower portion to be positioned in the basal bone and defining a second axis. The dental implant fixture may further include an intermediate offset-defining portion between the upper portion and the lower portion to define an offset between the first axis and the second axis so that the lower portion avoids the neurovascular bundle.

The upper portion, lower portion, and intermediate offset-defining portion of the dental implant fixture may be integrally formed as a monolithic unit. In addition, a cross-member may be carried by the intermediate offset-defining portion and/or the bottom portion for increased stability. The dental prosthesis may be connected to the upper portion of the dental implant fixture.

The dental implant fixture may taper downwardly in size towards an uppermost end thereof. The dental implant fixture may have a smooth inner surface.

The dental implantation system may also comprise a dental implant guide to facilitate positioning of the dental implant fixture in the patient's jawbone. In addition, the dental implantation system may further comprise a dental implantation unit for generating a specification for fabricating each of the dental implant fixture and the dental implant guide.

A method aspect of the invention is directed to a method for making a dental implantation system that may secure a dental prosthesis in a patient's jawbone. The jawbone may comprise an alveolar bone, a basal bone adjacent the alveolar bone, and a neurovascular bundle running through the jawbone. The method may comprise forming a dental implant fixture having an elongate shape and comprising an upper portion to be positioned in the alveolar bone to receive the dental prosthesis and defining a first axis. The method may also comprise forming a dental implant fixture having a lower portion to be positioned in the basal bone and defining a second axis. The method may further comprise forming an intermediate offset-defining portion between the upper portion and the lower portion to define an offset between the first axis and the second axis so that the lower portion avoids the neurovascular bundle.

DETAILED DESCRIPTION OF THE PREFERRED EMBODIMENTS

The invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout, and prime notation is used to indicate similar elements in alternative embodiments.

Figure 1:
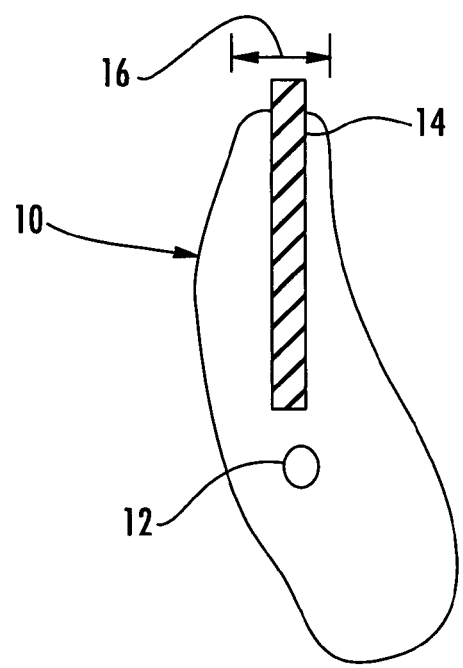
FIG. 1 is a transverse cross-sectional view of a patient's jawbone including a prior art dental implant fixture.
Figure 2:
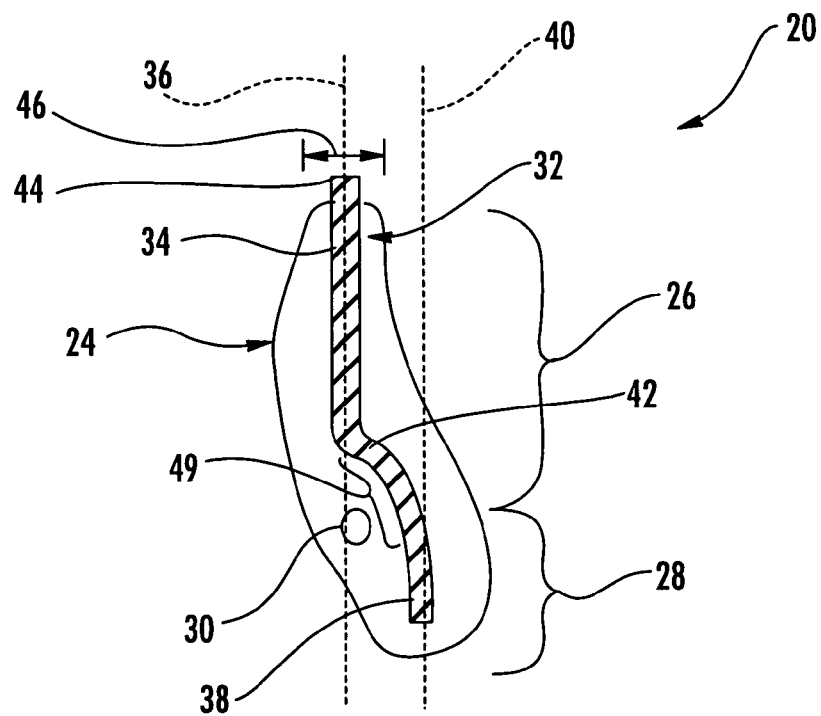
FIG. 2 is a transverse cross-sectional view of a patient's jawbone including a dental implant fixture in accordance with the invention
Figure 3:
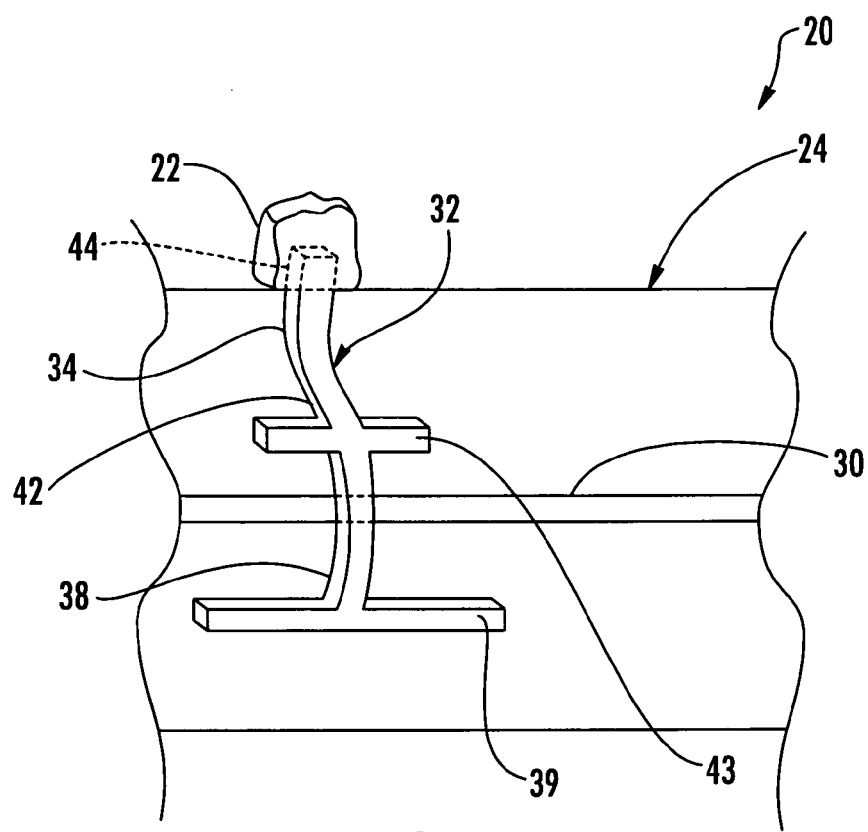
FIG. 3 is a longitudinal partial cross-sectional view of patient's jawbone including the dental implant fixture as shown in FIG. 2.

Referring initially to FIGS. 2 and 3, a dental implantation system 20 for securing a dental prosthesis 22 in a patient's jawbone 24 is described. The patient's jawbone 24 includes an alveolar bone 26, a basal bone 28 adjacent the alveolar bone, and a neurovascular bundle 30 running through the jawbone.

The dental implantation system 20 includes a dental implant fixture 32 having an elongate shape and including an upper portion 34 to be positioned in the alveolar bone 26 to receive the dental prosthesis 22 and defining a first axis 36. The dental implant fixture 32 also includes a lower portion 38 to be positioned in the basal bone 28 and defining a second axis 40. The dental implant fixture 32 further includes an intermediate offset-defining portion 42 between the upper portion 34 and the lower portion 38 to define an offset between the first axis 36 and the second axis 40 so that the lower portion avoids the neurovascular bundle 30. Accordingly, the dental implantation system 20 overcomes many of the shortcomings of conventional dental implant fixtures.

The upper portion 34, the lower portion 38, and the intermediate offset-defining portion 42 of the dental implant fixture 32 may be integrally formed as a monolithic unit, for example. In other embodiments, the dental implant fixture 32 may comprise at least two components joined together as will be appreciated by those of skill in the art.

The dental implant fixture 32 may also optionally include an intermediate cross-member 43 carried by the intermediate offset-defining portion 42. The dental implant fixture 32 may also optionally include a lower cross-member 39 carried by the lower portion 38. Of course, one or both of these cross-members 43, 39 may be integrally formed with the other portions of the dental implant fixture 32 as will be appreciated by those skilled in the art.

The dental prosthesis 22 may be advantageously connected to the upper portion 34 of the dental implant fixture 32 prior to the implantation of the dental implant fixture in the patient's jawbone 24. The dental prosthesis 22 may be connected to the upper portion 34 of the dental implant fixture 32 after the implantation of the dental implant fixture in the patient's jawbone 24, but on the same day the dental implant fixture is installed, for example.

Figure 4:
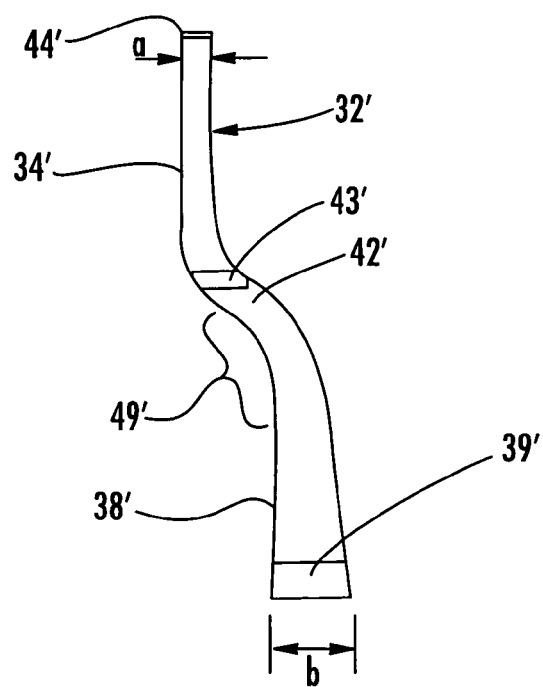
FIG. 4 is a side perspective view of an alternative embodiment of the dental implant fixture in accordance with the invention.

With additional reference to FIG. 4, an alternative embodiment of the dental implant fixture 32' is illustrated as tapering downwardly in size towards an uppermost end 44' of the dental implant fixture. In other words, the dimension "a" is smaller than the dimension "b" as will be appreciated by those of skill in the art. The taper permits the uppermost end 44' to have less surface area than the upper portion 34', the intermediate offset-defining portion 42', and/or the lower portion 38'. For example, the taper permits the narrow uppermost end 44' to compensate for a narrow ridge width 46 (see FIG. 2) of the patient's jawbone 24 while also permitting the upper portion 34', the intermediate offset-defining portion 42', and/or the lower portion 38' to have an increased surface area relative to the uppermost end 44'. This increased surface area of the upper portion 34', the intermediate offset-defining portion 42', and/or the lower portion 38' increases the anchoring surface of the dental implant fixture 32' to help compensate for the patient's narrow ridge width 46.

The dental implant fixture 32 illustratively has a smooth inner surface 49 along the intermediate offset portion 42 and extending downwardly to the lower portion 38. In other words, the dental implant fixture 32 may have a smooth inner surface 49 adjacent the neurovascular bundle 30. This smooth surface 49 may be less irritating if it contacts the neurovascular bundle 30, for example.

A dental implant guide, not shown, may be used to facilitate the installation of the dental implant fixture 32 as will be appreciated by those skilled in the art. Various exemplary guides are disclosed in U.S. Pat. No. 5,888,065 to Sussman and U.S. Pat. No. 6,869,283 also to Sussman, the entire contents of which are incorporated herein by reference.

Figure 5:
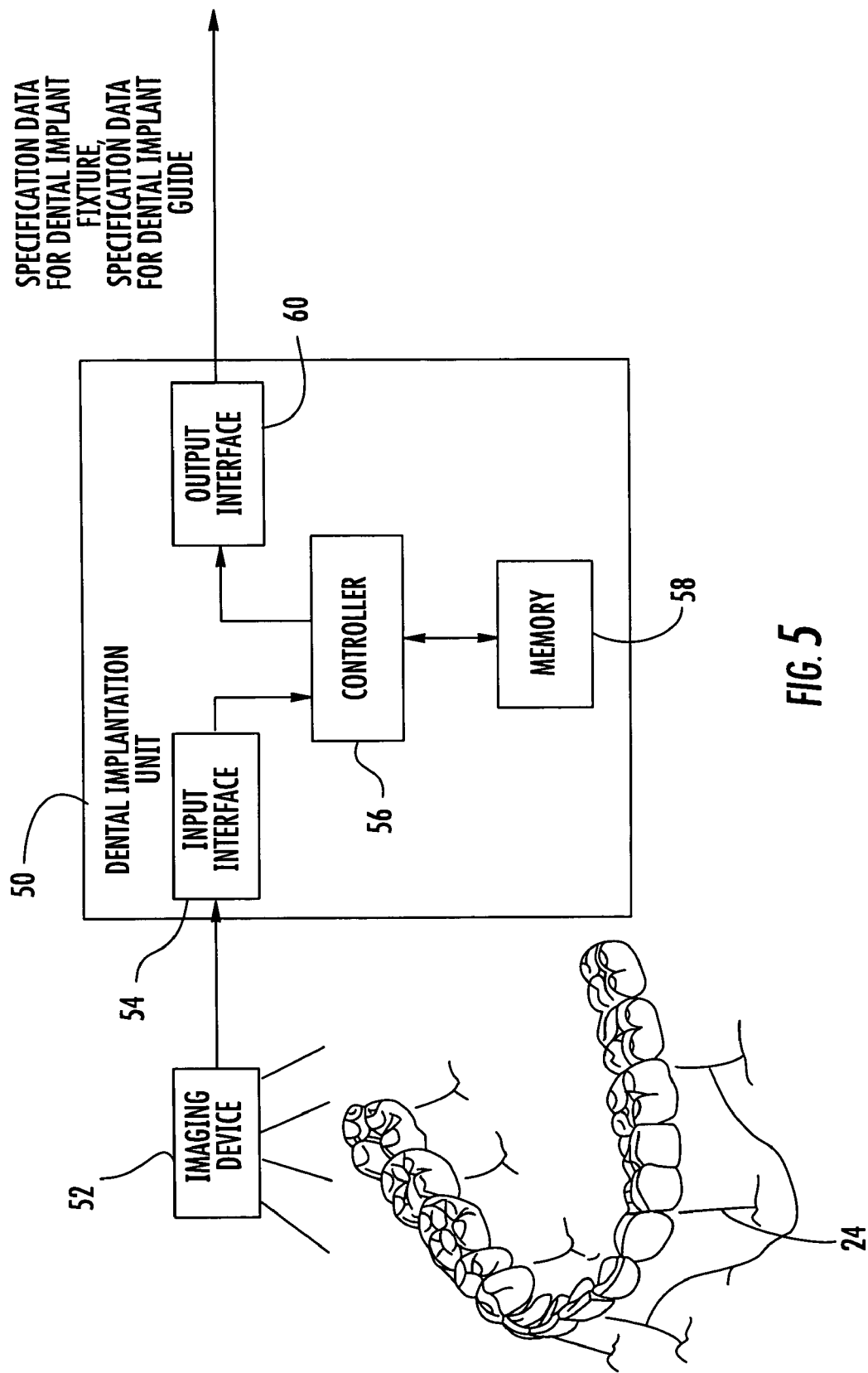
FIG. 5 is a block diagram of a dental implantation unit in accordance with the invention.

Referring now to FIG. 5, a dental implantation unit 50 used to facilitate the installation of the dental implant fixture 32 is now described. The dental implantation unit 50 is illustrated as comprising a controller 56 connected to an input interface 54, a memory 58, and output interface 60. The dental implantation unit 50 includes software and/or hardware for modeling imaging data generated by an imaging device 52 connected to the dental implantation unit.

The imaging device 52 may be a computed tomography unit or the like, for example. The imaging device 52 scans the patient's jawbone 24 to generate modeling data of the patient's jawbone. The dental implantation unit 50 uses the modeling data to generate a specification for fabricating the dental implant fixture 32. In addition, the dental implantation unit 50 uses the modeling data to generate a specification for the dental implant guide.

A method aspect of the invention is directed to a method for making a dental implantation system 20 for securing a dental prosthesis 22 in a patient's jawbone 24. The jawbone 24 comprises an alveolar bone 26, a basal bone 28 adjacent the alveolar bone, and a neurovascular bundle 30 running through the jawbone. The method may comprise forming a dental implant fixture 32 having an elongate shape and comprising an upper portion 34 to be positioned in the alveolar bone 26 to receive the dental prosthesis 22 and defining a first axis 36. The method may also comprise forming a dental implant fixture 32 having a lower portion 38 to be positioned in the basal bone 28 and defining a second axis 40. The method may further comprise an intermediate offset-defining portion 42 between the upper portion 34 and the lower portion 38 to define an offset between the first axis 36 and the second axis 40 so that the lower portion avoids the neurovascular bundle 30.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that other modifications and embodiments are intended to be included within the scope of the appended claims.

That which is claimed is:

1. A dental implantation system for securing a dental prosthesis in a patient's jawbone, the patient's jawbone comprising an alveolar bone, a basal bone adjacent the alveolar bone, and a neurovascular bundle running through the jawbone, the dental implantation system comprising:
a dental implant fixture having a elongate shape and comprising
an upper portion to be positioned in the alveolar bone to receive the dental prosthesis, defining a first axis,
a lower portion to be positioned in the basal bone, defining a second axis parallel to the first axis, and a curved intermediate offset-defining portion between the upper portion and the lower portion that defines an offset between the first axis and the second axis so that the lower portion avoids the neurovascular bundle, wherein the lower portion is offset from the first axis, and the second axis does not intersect the upper portion.

2. The dental implantation system according to claim 1 wherein said upper portion, lower portion, and curved intermediate offset-defining portion are integrally formed as a monolithic unit.

3. The dental implantation system according to claim 1 wherein said dental implant fixture further comprises an intermediate cross-member carried by said curved intermediate offset-defining portion.

4. The dental implantation system according to claim 1 wherein said dental implant fixture further comprises a bottom cross-member carried by said singular lower portion.

5. The dental implantation system according to claim 1 wherein said dental implant fixture tapers downwardly in size towards an uppermost end thereof.

6. The dental implantation system according to claim 1 wherein said dental implant fixture has a smooth surface.

7. The dental implantation system according to claim 1 further comprising a dental implantation unit for generating a specification for fabricating said dental implant fixture, and generating a specification for fabricating a dental implant guide.

8. A dental implantation system for a patient's jawbone, the patient's jawbone comprising an alveolar bone, a basal bone adjacent the alveolar bone, and a neurovascular bundle running through the jawbone, the dental implantation system comprising: a dental implant fixture having an elongate shape and comprising
an upper portion to be positioned in the alveolar bone to receive the dental prosthesis, defining a first axis, and comprising an upper end and a lower end, a singular lower portion to be positioned in the basal bone, defining a second axis parallel to the first axis, and comprising an upper end and lower end,
a curved intermediate offset-defining portion between the upper end of the singular lower portion and the lower portion that defines an offset between the first axis and the second axis so that the lower portion avoids the neurovascular bundle, wherein the lower portion is offset from the first axis, and the second axis does not intersect the upper portion, and a dental prosthesis connected to an upper end of the upper portion of said dental implant fixture.

9. The dental implantation system according to claim 8 wherein said upper portion, lower portion, and curved intermediate offset-defining portion are integrally formed as a monolithic unit.

10. The dental implantation system according to claim 8 wherein said dental implant fixture further comprises: an intermediate cross-member carried by said curved intermediate offset-defining portion; and a bottom cross-member carried by said singular lower portion.

11. The dental implantation system according to claim 8 wherein said dental implant fixture tapers downwardly in size towards an uppermost end thereof.

12. The dental implantation system according to claim 8 wherein said dental implant fixture has a smooth inner surface.

13. The dental implantation system according to claim 8 further comprising a dental implantation unit for generating a specification for fabricating said dental implant fixture, and generating a specification for fabricating a dental implant guide.

14. A method for making a dental implantation system that secures a dental prosthesis in a parient's jawbone, the patient's jawbone comprising an alveolar bone, a basal bone adjacent the alveolar bone, and a neurovascular bundle running through the jawbone, the method comprising:
forming a dental implant fixture having an elongate shape and comprising
an upper portion to be positioned in the alveolar bone to receive the dental prosthesis, defining a first axis, a lower portion to be positioned in the basal bone, defining a second axis parallel to the first axis, and
a curved intermediate offset-defining portion between the upper portion and lower portion that defines an offset between the first axis and the second axis so that the singular lower portion avoids the neurovascular bundle, wherein the lower portion is offset from the first axis, and the second axis does not intersect the upper portion.

15. The method according to claim 14 wherein the upper portion, singular lower portion and curved intermediate offset-defining portion are integrally formed as a monolithic unit.

16. The method according to claim 14 further comprising; forming an intermediate cross-member carried by the curved intermediate offset-defining portion; and forming a bottom cross-member carried by the lower portion.

17. The method according to claim 14 further comprising connecting a dental prosthesis to the upper portion of the dental implant fixture.

18. The method according to claim 14 wherein the dental implant fixture tapers downwardly in size towards an uppermost end thereof.

19. The method according to claim 14 wherein the dental implant fixture has a smooth surface.

20. The method according to claim 14 further comprising positioning the dental implant fixture in the patient's jawbone using a dental implant guide.

21. The method according to claim 20 further comprising generating specifications for fabricating the dental implant fixture and the dental implant guide using a dental implantation unit.

* * * * *